(12) United States Patent
Thelen

(10) Patent No.: US 10,088,033 B2
(45) Date of Patent: Oct. 2, 2018

(54) DRIVE MECHANISM FOR A SPIN TEST RIG

(71) Applicant: Schenck RoTec GmbH, Darmstadt (DE)

(72) Inventor: Dieter Thelen, Modautal (DE)

(73) Assignee: Schenck RoTec GmbH, Darmstadt (DE)

(*) Notice: Subject to any disclaimer, the term of this patent is extended or adjusted under 35 U.S.C. 154(b) by 321 days.

(21) Appl. No.: 15/016,708

(22) Filed: Feb. 5, 2016

(65) Prior Publication Data

US 2016/0230873 A1 Aug. 11, 2016

(30) Foreign Application Priority Data

Feb. 10, 2015 (DE) .................... 10 2015 101 885

(51) Int. Cl.
| | |
|---|---|
| *F16H 57/021* | (2012.01) |
| *F16H 57/028* | (2012.01) |
| *F16H 1/28* | (2006.01) |
| *G01N 3/16* | (2006.01) |

(52) U.S. Cl.
CPC ......... *F16H 57/021* (2013.01); *F16H 57/028* (2013.01); *F16H 1/28* (2013.01); *G01N 3/165* (2013.01)

(58) Field of Classification Search
CPC ........ F16H 57/021; F16H 57/028; F16H 1/28; G01N 3/165
See application file for complete search history.

(56) References Cited

U.S. PATENT DOCUMENTS 2,129,992 A * 9/1938 De Mattia ................. B04B 1/20
                                                            384/195
3,138,021 A 6/1964 Linn
3,851,819 A 12/1974 Tadokoro
(Continued)

FOREIGN PATENT DOCUMENTS

| DE | 1 125 206 B | 3/1962 |
|---|---|---|
| DE | 2 337 600 A1 | 2/1974 |

(Continued)

OTHER PUBLICATIONS

Printout from Wikipedia "Umlaufrädergetriebe" Version Jan. 9, 2015 (total of 10 pages).

(Continued)

*Primary Examiner* — David M Fenstermacher
(74) *Attorney, Agent, or Firm* — Collard & Roe, P.C.

(57) ABSTRACT

Disclosed is a drive mechanism for driving a spin test rig, comprising a transmission casing (1) which accommodates a transmission gear unit (8) having a vertical output shaft (10) and an input shaft (9) coaxial therewith. The output shaft (10) has an upper end arranged in the transmission gear unit (8) and a lower end adapted to be coupled to a test object. The transmission casing (1) includes a casing lower part (4) detachable therefrom with the gear unit installed, in which casing part the output shaft (10) is axially and radially carried in bearings (28, 29) at a distance from its ends. The transmission gear unit (8) is configured such that the output shaft (10), together with the casing lower part (4) and the bearings arranged therein, is removable from the transmission casing (1).

10 Claims, 1 Drawing Sheet

(56) References Cited

U.S. PATENT DOCUMENTS

| | | | | |
|---|---|---|---|---|
| 4,577,716 A | * | 3/1986 | Norton | B62D 5/0466 |
| | | | | 180/444 |
| 4,656,409 A | * | 4/1987 | Shimizu | B62D 5/0403 |
| | | | | 180/444 |
| 4,660,669 A | * | 4/1987 | Shimizu | B60G 21/0553 |
| | | | | 180/444 |
| 6,149,573 A | * | 11/2000 | Berger | B04B 9/146 |
| | | | | 494/55 |
| 6,255,751 B1 | * | 7/2001 | Hoffmann | H02K 7/083 |
| | | | | 310/40 MM |
| 6,355,996 B1 | * | 3/2002 | Birkestrand | B60L 11/1807 |
| | | | | 180/65.51 |
| 6,478,724 B1 | * | 11/2002 | Beattey | B04B 9/08 |
| | | | | 494/55 |
| 6,615,670 B2 | | 9/2003 | Shibasaki et al. | |
| 6,997,860 B2 | * | 2/2006 | Opfer | B04B 9/08 |
| | | | | 494/55 |
| 2010/0210391 A1 | * | 8/2010 | Dinger | B64C 13/28 |
| | | | | 475/149 |
| 2016/0333965 A1 | * | 11/2016 | Shen | F16H 37/0833 |

FOREIGN PATENT DOCUMENTS

| | | |
|---|---|---|
| DE | 102 06 950 A1 | 9/2002 |
| DE | 10 2010 012 780 A1 | 9/2011 |
| GB | 920 567 A | 3/1963 |

OTHER PUBLICATIONS

Printout from Wikipedia "Umlaufrädergetriebe" Version Jan. 9, 2015 (total of 10 pages) with English abstract.

\* cited by examiner

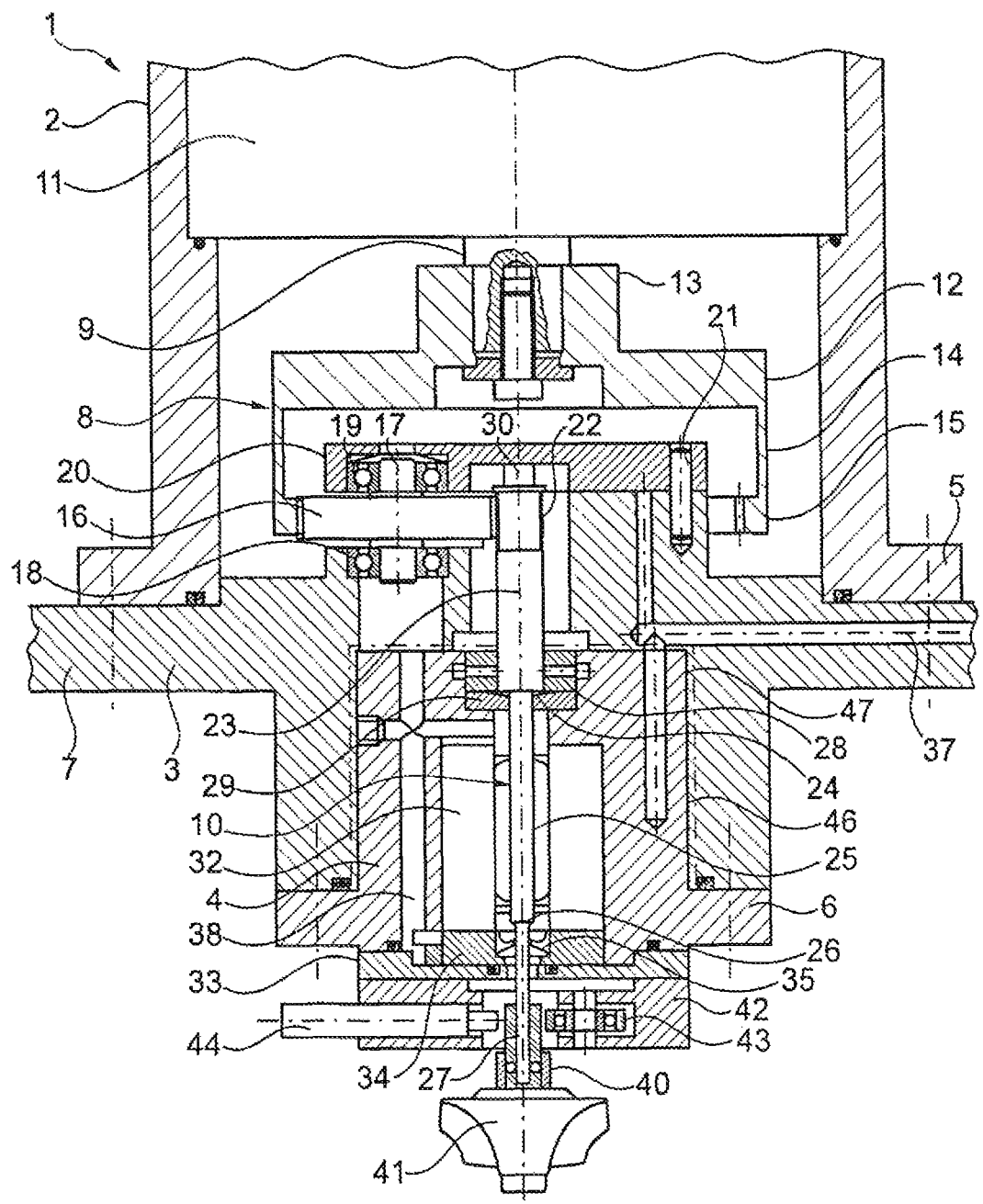

DRIVE MECHANISM FOR A SPIN TEST RIG

CROSS REFERENCE TO RELATED APPLICATIONS

Applicants claim priority under 35 U.S.C. § 119 of German Patent Application No. 10 2015 101 885.3 filed Feb. 10, 2015.

FIELD OF THE INVENTION

This invention relates to a drive mechanism of a spin test rig having a transmission comprising a transmission casing which accommodates a transmission gear unit having a vertical output shaft and an input shaft coaxial therewith, with the output shaft having an upper end associated with the transmission gear unit and a lower end for connection with a test object.

BACKGROUND OF THE INVENTION

Spin test rigs are machines for testing the strength of machine parts rotating at high speeds, including, for example, rotors of turbines, compressors, high-speed electric motors, clutches, etc. A test rig of this type is known from DE 11 25 206 B.

DE 102 06 950 A1 further describes a high-speed rotation testing apparatus having a spindle holding a test object at its lower end, a driving motor for applying torque to the spindle, and a frame for supporting a rotor shaft of the driving motor. The shaft is arranged in the vertical direction of the apparatus, with the spindle being driven directly by coupling the upper ends of the rotor shaft and the spindle. A damping mechanism to limit vibration is provided in the vicinity of the lower end of the spindle. In a further embodiment, the high-speed rotation testing apparatus has a second spindle connected to the first spindle via a coupling so that their central axes are aligned with each other and the spindles rotate jointly. Extending from the first spindle, the second spindle extends downward and is in engagement with a weight supporting shaft and the damping mechanism, with the weight supporting shaft being supported by the casing by means of thrust bearings. The test object is secured to the lower end of the second spindle by means of a holding device.

Testing such rotors is performed at a test speed significantly higher than the maximum operating speed of the rotors. To fulfill their test task, spin test rigs therefore require a drive mechanism for very high rotational speeds. Drive mechanisms are known which use a transmission gear unit for generation of the high rotational speeds.

When testing rotors at overspeed, the test object is often subject to intentional or unintentional bursting. However, before the test object undergoes complete disintegration on account of centrifugal action, mass elements in the rotating test object tend to become displaced, thereby causing very large imbalances and, in consequence, high vibration amplitudes of the drive shaft supporting the test object. There exists therefore the demand for allowing large vibration amplitudes. In view of this requirement, spin test rigs have been developed reflecting a configuration in which the test object is mounted on a comparatively thin and hence highly elastic, vertically arranged shaft referred to as the spin shaft, hi addition, the spin shaft may be guided through a special, yielding damper bearing. By virtue of the elasticity of the spin shaft and the yielding nature of the damper bearing, the spin rig is capable of withstanding large vibration amplitudes in the presence of high rotational speeds.

When a spin test rig is configured to make allowance for the dynamics of the test object and the spin shaft, this results in a certain handling complexity regarding assembly and preparation of the test object for the spin test. Awkward handling proves to be a disadvantage particularly when the test object needs to be equipped with sensing devices for measurements during the spin test, which occurs frequently. Such measurements may be taken, for example, of temperatures and tensile stresses of the test object. To improve handling, known drive mechanisms for spin test rigs allow the spin shaft to be removed and, upon connection with the test object, to be replaced in the drive mechanism. Implementation of this design is, however, not always possible. Particularly in cases where small drive mechanisms rotating at very high speeds are used, reasons of geometry and strength forbid the removal of the spin shaft.

SUMMARY OF THE INVENTION

It is an object of the present invention to provide a drive mechanism of a spin test rig of the type referred to with a transmission which is suitable for a small drive mechanism rotating at very high speed and which, for greater ease of handling, enables the spin shaft, which is adapted for coupling to the test object, to be removed from the transmission.

According to the invention the object is accomplished by a drive mechanism of a spin test rig comprising a transmission having a transmission casing accommodating a transmission gear unit which has a vertical output shaft and an input shaft coaxial therewith, wherein the output shaft has an upper end associated with the transmission gear unit and a lower end adapted to be coupled to a test object, wherein the transmission casing includes a casing lower part that is detachable from the transmission casing while the transmission is installed in the spin test rig, and the output shaft is axially and radially carried in the casing lower part by bearings placed at a distance from the upper and lower end of the output shaft, and wherein the transmission gear unit is configured such that the output shaft, together with the casing lower part and the bearings arranged therein, is removable from the transmission casing downwardly in the direction of the axis of the output shaft.

In the drive mechanism of the present invention, the removal of the output shaft adapted to be coupled to the test object and defining the spin shaft is made possible by detaching and removing a casing lower part which houses exclusively the bearings of the output shaft. This part of the casing is flange-mounted on the transmission casing from below and detachable from the installed transmission together with the output shaft once the flange coupling is disengaged. Following removal of the unit, as separated from the transmission and comprised of casing lower part and output shaft, from the spin test rig, the operations of mounting the test object on the output shaft and preparing it are accomplishable in a straightforward manner. In the process, the output shaft remains in the casing part supporting it and removed as a unit, whereby it is protected against damage when attaching the test object. This protection enables the port n of the output shaft adjacent to the test object to be very thin, which affords the desired advantages when very small rotors are spin tested at high test speeds.

According to another proposal of the invention, the transmission gear unit is a planetary gear unit wherein the input shaft carries an annulus having its inner ring gear in meshing engagement with planet gears supported in the transmission casing and wherein a sun gear cooperating with the planet gears is formed by an upper end section of the output shaft provided with external gear teeth. This configuration of the transmission gear unit is conducive to the removal of the output shaft from the transmission in addition to enabling a straightforward design of the output shaft with a small diameter and suitable for very high rotational speeds.

According to still another proposal of the invention, the output shaft integrally made of one piece includes an upper section defining the sun gear, a middle section of a diameter smaller than the first section, and a lower section of a diameter smaller than the middle section. Preferably, a bearing collar for axially supporting the output shaft is formed between the upper and the middle section of the output shaft. This configuration of the output shaft affords ease of manufacture in addition to exhibiting the diameter suited to the individual spheres of operation. Whilst it is desirable for the diameter on the sun gear and in the area of the bearing support to be not too small, the reduced diameters of the middle and lower sections provide for the desired elasticity and a reduction of the friction moment.

The bearing arrangement of the output shaft the casing lower part preferably includes a radial plain bearing carrying the upper section, an axial thrust bearing cooperating with the bearing collar, and a damper bearing surrounding the middle section. In this arrangement, the output shaft is advantageously arranged in the transmission casing in such a way that only the lower section protrudes from the transmission casing through a casing opening provided with a seal. Arranging the seal on the lower section of the output shaft has the advantage that the load imposed on the seal is kept at a minimum on account of the reduced diameter prevailing at this particular location.

According to another proposal of the invention, the end of the output shaft protruding from the transmission casing extends through a retaining device intended to prevent excessive radial vibrations of the output shaft. The retaining device preferably includes a plurality of antifriction bearings arranged around the output shaft with axes of rotation parallel to the output shaft, with the antifriction bearings having rotary outer races whose envelope surfaces are spaced from the output shaft. In addition, the retaining device may be provided, with a broadband sensor for monitoring the vibrations of the output shaft.

BRIEF DESCRIPTION OF THE DRAWING

The present invention will be described in more detail in the following with reference to a preferred embodiment of the invention illustrated in the accompanying drawing. The drawing shows a cross-section through a transmission intended for use with a spin test rig.

DETAILED DESCRIPTION OF THE DRAWING

The transmission illustrated in the drawing comprises a transmission casing 1 fixedly connectable with a machine column and composed of a casing upper part 2, a casing center part 3 and a casing lower part 4. The casing upper part 2 and the casing lower part 4 are provided with a flange 5 and 6, respectively for fixedly securing them to the casing center part 3 by means of screws. Seals arranged on the flanges 5, 6 effect a tight seal on the joints. The casing center part 3 has a plate-shaped portion 7 extending outwardly beyond the flange 5 and serving to fasten the casing in a test rig.

The transmission casing 1 surrounds a chamber accommodating a transmission gear unit 8 designed as a planetary gear unit having an input shaft 9 and an output shaft 10. The axes of the input shaft 9 and the output shaft 10 are in relative alignment vertically and coaxially. The input shaft 9 is formed by a drive spindle carried for rotation in a spindle housing 11 installed in the casing upper part 2. The drive spindle may be driven in a variety of ways, either directly or via a transmission, for example, a traction drive, an electric motor, or a turbine.

The transmission-mounted end of the input shaft 9 carried in the spindle housing 11 supports an annulus 12 whose hub 13 is connected with the input shaft 9 in a manner preventing relative rotation and secured axially to a shoulder of the input shaft 9 by means of a screw and a stepped washer. The annulus 12 includes a cylindrical annulus sleeve 14 carrying at its end remote from the hub a ring gear 15 with internal gearing. The ring gear 15 is in meshing engagement with three planet gears 16 constructed as spur gears spaced from each other by a regular distance and mounted in the casing center part 3 for rotation about axes parallel to the axis of the input shaft 9. The drawing shows only one of the planet gears 16, but it will be understood that all three planet gears are of like construction.

As becomes apparent from the drawing, the planet gear 16 shown has on either side a bearing journal 17 carried in an antifriction bearing 18 and 19, respectively. The lower antifriction bearing 18 is arranged in a receiving bore in the casing part 4. The upper antifriction bearing 19 is arranged in a receiving bore in a cover part 20 which is secured to the casing part 3 in accurate alignment by means of screws, not shown, and dowel pins 21.

The sun gear 22 cooperating with the planet gears 16 of the transmission gear unit 8 is formed by the externally toothed upper end of the integrally formed output shaft 10. This enables the sun gear to be built to a small diameter and avoids strength-related shortcomings of a non-bonded connection between sun gear and shaft. The output shaft 10 has an upper section 23 extending from the teeth of the sun gear with constant diameter up to a bearing collar 24 which is adjoined by a middle section 25 of a diameter smaller than the section 23. Adjoining the middle section 25 in downward direction on a step 26 is a lower section 27 of a diameter smaller than the middle section 25.

The upper section 23 of the output shaft 10 is received in a bore of the casing center part 3 of an inner diameter significantly larger than the outer diameter of the section 23. The output shaft 10 is therefore readily insertable into, and removable from, the casing part 3 without any contact between the output shaft 10 and the casing part 3 occurring. The lower end of the section 23 of the output shaft 10 is radially carried in a radial plain bearing 28, and with the bearing collar 24 axially in an axial thrust bearing 29. The axial thrust bearing 29 supports the output shaft 10 only downwardly in the direction of gravity. In view of the vertical arrangement of the shaft, it is not necessary to provide for bearing support in the opposite direction. Any excessive movement of the output shaft 10 in upward direction is limited by a stop element 30 mounted on the cover part 20.

The bearing arrangement comprised of axial thrust and radial plain bearings 28, 29 is housed in the casing lower part 4. Underneath this bearing arrangement, it also houses a damper bearing 32 which surrounds the middle section 25 of the output shaft 10 and cooperates therewith. Being yielding in radial direction, the damper bearing 32 serves to dampen radial vibrations of the middle section 23 of the elastic output shaft 10. In this manner it is possible to control relatively large vibration amplitudes of the output shaft 10 in the presence of high rotational speeds.

The damper bearing 32 is accommodated in a cylindrical chamber of the casing part 4 which has its lower open end closed by a cover 33 secured to the casing part 4. The cover 33 has a central opening through which the lower section 27 of the output shaft 10 is passed. The opening in the cover 33 is sufficiently large to enable the section 27 to vibrate freely.

Arranged in the casing part 4 between the cover 33 and the damper bearing 32 is an annular disk 34 carrying a vacuum seal 35 engaging the section 27 fluid-tight. Additional ring seals effect a tight seal between the annular disk 34 and the cover 33 and between the cover 33 and the casing part 4. In this manner, the interior space of the transmission casino 1 is vacuum-sealed at the exit end of the output shaft 10. This is necessary because in a spin test rig the lower end of the transmission casing 1 may serve as boundary of a vacuum chamber which surrounds the test object during the spin test.

The gears of the transmission gear unit 8, its bearings and the bearings of the output shaft 10 are lubricated with a liquid lubricant fed via a supply line 37 in the casing part 3, reaching the individual lubricating points within the transmission casing 1 via distribution bores not shown in greater detail. Any excess of lubricant is discharged through a return line 38.

As shown in the drawing, a holding fixture 40 for receiving a test object 41 may be coupled by positive engagement by means of a shaft coupling to the end of the lower section 27 of the output shaft 10 protruding from the cover 33. The holding fixture 48 has a cylindrical shank with a central bore receiving the shaft end. The shank of the holding fixture 40 is surrounded by a retaining device 42 mounted on the underside of the cover 33. The retaining device 42 comprises three retainer bearings 43 formed by antifriction bearings spaced at regular intervals from each other and at a distance from the shank of the holding fixture 40. The retainer bearings 43 are capable of preventing excessive radial vibrations of the holding fixture 40.

The retaining device 42 further comprises a broadband sensor 44 for monitoring the vibrations of the holding fixture 40 during the spin test run of a test object.

A feature affording great advantages for use of the transmission of the invention in a spin test rig comprises the possibility of removing the output shaft 10 with its bearing support from the transmission casing 1 in easy manner, although the transmission is built into a spin test rig where it remains. To afford this possibility, the bearings of the output shaft 10, that is, the radial plain bearing 28, the axial thrust bearing 29 and the damper bearing 32 and also the vacuum seal 35 are completely arranged in the casing lower part 4, and the casing lower part 4 is inserted into the casing center part 3 from below such as to be removable from the casing part 3 in the direction of the axis of the output shaft 10 once the screws securing the flange 6 to the casing part 3 are unscrewed.

The casing part 4 has a cylindrical envelope surface 46 guiding it in a receiving bore 47 in the casing part 3, thereby securing it against tilting and canting when detaching and replacing the casing part 3. The risk of damaging the output shaft 10 when removing it from the transmission and replacing it is thereby eliminated. The use of beveled tooth edges on the frontal surface of the sun gear 22 enables engagement of the sun gear teeth with the tooth spaces of the planet gears to be facilitated.

Furthermore, the sun gear 22 driving the output shaft 10 is configured and arranged in such a way as to enable it to be withdrawn from, and reinstalled into, the transmission together with the output shaft 10. This is favored by constructing the transmission gear unit as planetary gear unit according to the known Stoeckicht principle. According to this principle, the sun gear requires no bearing support of its own, floating instead, so to speak, between the planet gears which locate it centrally. Removal and replacement of the sun gear are therefore not obstructed by an additional bearing. Preferably, the sun gear is formed integrally with the output shaft 10, as shown in the drawing. This permits a small sun gear diameter and a high transmission ratio to achieve high rotational speeds of the output shaft.

The transmission described furthermore distinguishes itself by its straightforward and compact construction in addition to enabling, owing to its favorable load distribution, the sun gear and the output shaft 10 to be built to small diameters. The floating arrangement of the sun gear and the bearing support of the upper end of the output shaft formed by it produce a favorable rotor-dynamic behavior allowing extremely high rotational speeds of the output shaft 10. Owing to the stepwise reduction of the diameter of the output shaft without sacrificing the strength, a bearing support suitable for high rotational speeds, a favorable vibratory response and a high elasticity desired for light weight test objects are accomplished.

What is claimed is:

1. A drive mechanism of a spin test rig comprising a transmission having a transmission casing accommodating a transmission gear unit which has a vertical output shaft and an input shaft coaxial therewith,
   wherein the output shaft has an upper end associated with the transmission gear unit and a lower end adapted to be coupled to a test object,
   wherein the transmission casing includes a casing lower part that is detachable from the transmission casing while the transmission is installed in the spin test rig, and the output shaft is axially and radially carried in the casing lower part by bearings placed at a distance from the upper and lower end of the output shaft,
   wherein the bearings of the output shaft are completely arranged in the casing lower part, and
   wherein the transmission gear unit is configured such that the output shaft, together with the casing lower part and the bearings arranged therein, is removable from the transmission casing downwardly in the direction of the axis of the output shaft.

2. The drive mechanism according to claim 1, wherein the transmission gear unit is a planetary gear unit wherein the input shaft carries an annulus having its inner ring gear in meshing engagement with a plurality of planet gears supported in the transmission casing and wherein a sun gear cooperating with the planet gears is formed by an upper end section of the output shaft provided with external gear teeth.

3. The drive mechanism according to claim 2, wherein the output shaft is integrally made of one piece and includes an upper section defining the sun gear, a middle section of a diameter smaller than the upper section, and a lower section of a diameter smaller than the middle section.

4. The drive mechanism according to claim 3, wherein a bearing collar for axially supporting the output shaft is formed between the upper and the middle section of the output shaft.

5. The drive mechanism according to claim 4, wherein the bearing of the output shaft in the casing lower part includes a radial plain bearing carrying the upper section, an axial thrust bearing cooperating with the bearing collar, and a yielding damper bearing surrounding the middle section.

6. The drive mechanism according to claim 1, wherein the output shaft is arranged in the transmission casing in such a way that a lower section of the output shaft protrudes from the transmission casing through a casing opening and that the casing opening is sealed relative to the lower section by means of a seal.

7. The drive mechanism according to claim 1, wherein the lower end of the output shaft protruding from the transmission casing extends through a retaining device designed to prevent excessive radial vibrations of the output shaft.

8. The drive mechanism according to claim 7, wherein the retaining device is provided with a broadband sensor for monitoring the vibrations of the output shaft.

9. The drive mechanism according to claim 7, wherein the retaining device includes a plurality of antifriction bearings arranged around the output shaft with axes of rotation parallel to the output shaft, said antifriction bearings having rotary outer races whose envelope surfaces are arranged at a distance from the output shaft.

10. The drive mechanism according to claim 1, wherein the input shaft is formed by a drive spindle carried for rotation in a spindle housing installed in the casing upper part.

* * * * *